United States Patent
Privitera et al.

(10) Patent No.: US 10,945,894 B2
(45) Date of Patent: Mar. 16, 2021

(54) DEVICES AND METHODS FOR DIRECTING A MEDICAL FABRIC INTO A PORTION OF THE BODY

(71) Applicant: University of Cincinnati, Cincinnati, OH (US)

(72) Inventors: Mary Beth Privitera, Mason, OH (US); Arthur Pancioli, Mason, OH (US)

(73) Assignee: University of Cincinnati, Cincinnati, OH (US)

( * ) Notice: Subject to any disclaimer, the term of this patent is extended or adjusted under 35 U.S.C. 154(b) by 652 days.

(21) Appl. No.: 14/434,544

(22) PCT Filed: Oct. 9, 2013

(86) PCT No.: PCT/US2013/064086
§ 371 (c)(1),
(2) Date: Apr. 9, 2015

(87) PCT Pub. No.: WO2014/058992
PCT Pub. Date: Apr. 17, 2014

(65) Prior Publication Data
US 2015/0283005 A1    Oct. 8, 2015

Related U.S. Application Data (60) Provisional application No. 61/711,480, filed on Oct. 9, 2012.

(51) Int. Cl.
*A61F 15/00* (2006.01)
*A61F 13/38* (2006.01)
(Continued)

(52) U.S. Cl.
CPC ............. *A61F 15/001* (2013.01); *A61F 13/38* (2013.01); *A61F 15/002* (2013.01); *A61F 2013/00302* (2013.01); *A61F 2013/2014* (2013.01)

(58) Field of Classification Search
CPC ...... A61F 15/001; A61F 15/002; A61F 13/38; A61F 2013/00302; A61F 2013/2014
See application file for complete search history.

(56) References Cited

U.S. PATENT DOCUMENTS 5,263,927 A * 11/1993 Shlain .............. A61B 17/00234
604/13
7,837,705 B2    11/2010 White et al.
(Continued)

FOREIGN PATENT DOCUMENTS

| EP | 0604101 A1 | 6/1994 |
|----|------------|--------|
| WO | 93/08740 A1 | 5/1993 |
| WO | 01/21058 | 3/2001 |

OTHER PUBLICATIONS

International Searching Authority, International Search Report and Written Opinion in corresponding Application No. PCT/US2013/064086, dated Jan. 22, 2014 (10 pages).
(Continued)

*Primary Examiner* — Benjamin J Klein
(74) *Attorney, Agent, or Firm* — Wood Herron & Evans LLP (57) ABSTRACT

A device (10) for directing a medical fabric (28) into a portion of a body. An elongated housing (12) having a distal end (16) and an opening (22) at the distal end (16). A supply of medical fabric (28) in the housing (12). An actuator (24) spaced from said opening (22) and configured to advance a portion of the medical fabric (28) through said housing (12) and out of the opening (22).

11 Claims, 7 Drawing Sheets

(51) Int. Cl.
  *A61F 13/20* (2006.01)
  *A61F 13/00* (2006.01)

(56) References Cited

U.S. PATENT DOCUMENTS

| | | |
|---|---|---|
| 2003/0015203 A1 | 1/2003 | Makower et al. |
| 2006/0161199 A1 | 7/2006 | Peterson |
| 2007/0179510 A1 | 8/2007 | Stone |
| 2007/0191753 A1* | 8/2007 | Wendorf ............... A61F 15/001 602/58 |
| 2010/0168514 A1 | 7/2010 | Callister et al. |
| 2011/0179610 A1* | 7/2011 | Catallo .................. D06C 21/00 26/18.6 |

OTHER PUBLICATIONS

Chinese Patent Office, Office Action issued in corresponding Chinese Patent Application No. 20138006204.8, English translation, dated Jun. 7, 2017 (4 pages).

Japanese Patent Office, English Trranslation of Office Action issued in corresponding JP Application No. 2015-536857, dated Sep. 11, 2017 (5 pages).

European Patent Office, Official Letter issued in corresponding European Application No. 13783161.6, dated Nov. 6, 2017, 8 pages.

* cited by examiner

DEVICES AND METHODS FOR DIRECTING A MEDICAL FABRIC INTO A PORTION OF THE BODY

RELATED APPLICATION

The present application claims priority to U.S. Ser. No. 61/711,480, filed Oct. 9, 2012, the disclosure of which is hereby incorporated herein by reference in its entirety.

FIELD OF THE INVENTION

The disclosure generally relates to treating abscesses and other wounds and, more specifically, to the packing of abscesses or other wounds with medical fabric such as gauze.

BACKGROUND OF THE INVENTION

An abscess is a collection of pus that has accumulated within a tissue due to an inflammatory response to infectious or foreign materials. An abscess forms to prevent the spread of infection to other parts of the body. Because the abscess essentially forms a wall or cavity between itself and the rest of the body, antibiotics and the natural defenses of the immune system are usually prevented from attacking the infection. Therefore, in order to cure an abscess, a clinician first incises the abscess and drains the collection of pus. The clinician then packs the abscess with gauze. The clinician grabs an amount of gauze with a hemostat, forceps, or other instrument and pushes the gauze into the abscess until the clinician feels a sufficient amount of gauze has been put into the abscess.

There are problems associated with this "grab and push" method of treatment. First, the grab and push procedure requires the physician to use both hands or requires the help of another clinician. For example, the physician must grab an amount of gauze with one hand and another hand is needed to cut the gauze to the desired length. Moreover, because the gauze frequently becomes stuck to the teeth or other gripping surface of the instrument, a portion of the packed gauze often exits from the abscess as the clinician retracts the instrument from the abscess, yet again requiring the use of an additional hand or hands. There is therefore a need in the art for a device and method of packing an abscess or other wound that addresses these and other problems.

SUMMARY OF THE INVENTION

In that regard, rather than relegating a clinician to the grab and push method, a device for directing a medical fabric into a portion of a body is provided and, in one embodiment, includes an elongated housing having a distal end and an opening at the distal end. The device includes a supply of medical fabric in the housing, and an actuator spaced from said opening and configured to advance a portion of the medical fabric through said housing and out of the opening.

In an alternative embodiment, a device for directing a medical fabric into a portion of a body includes an elongated housing configured to hold a supply of the medical fabric and an actuator spaced from the opening and coupled to the housing. The actuator is movable relative to the housing to advance a portion of the medical fabric through and out of the housing. The device further includes a probe at the distal end adapted for removing loculations.

A method of directing a medical fabric into a portion of a body is also provided and includes directing a distal end of a device having a rigid housing with medical fabric therein into a portion of the body, the device having an opening at the distal end, and actuating an actuator to engage the medical fabric to advance a portion of the medical fabric out of the opening and into the portion of the body.

DETAILED DESCRIPTION OF THE INVENTION

Figure 1A:
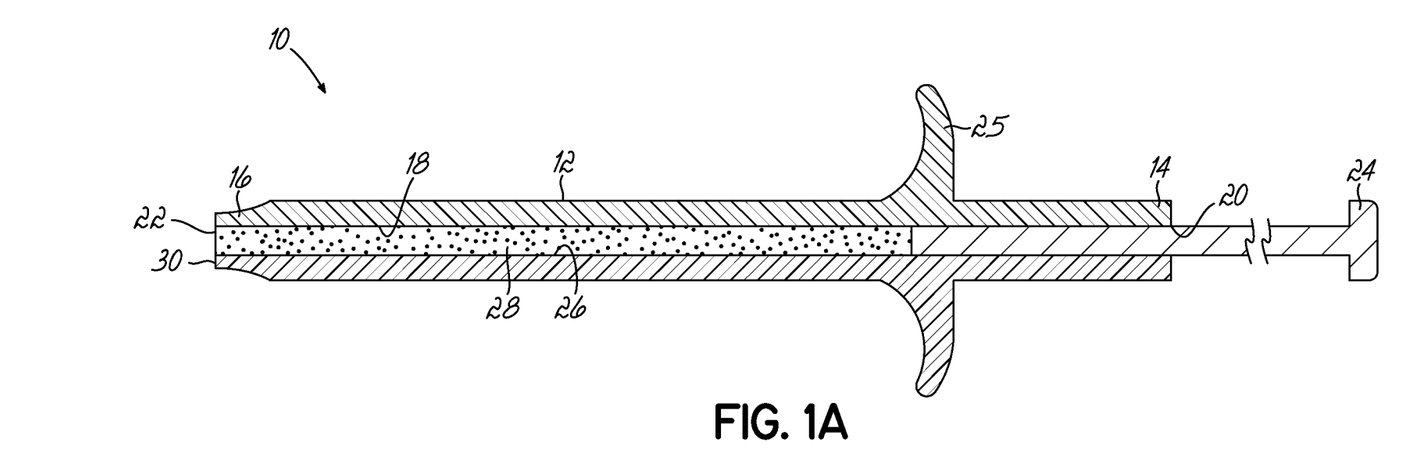
FIG. 1A is a cross-sectional view of a device for directing a medical fabric into a portion of the body, shown in a first position.
Figure 1B:
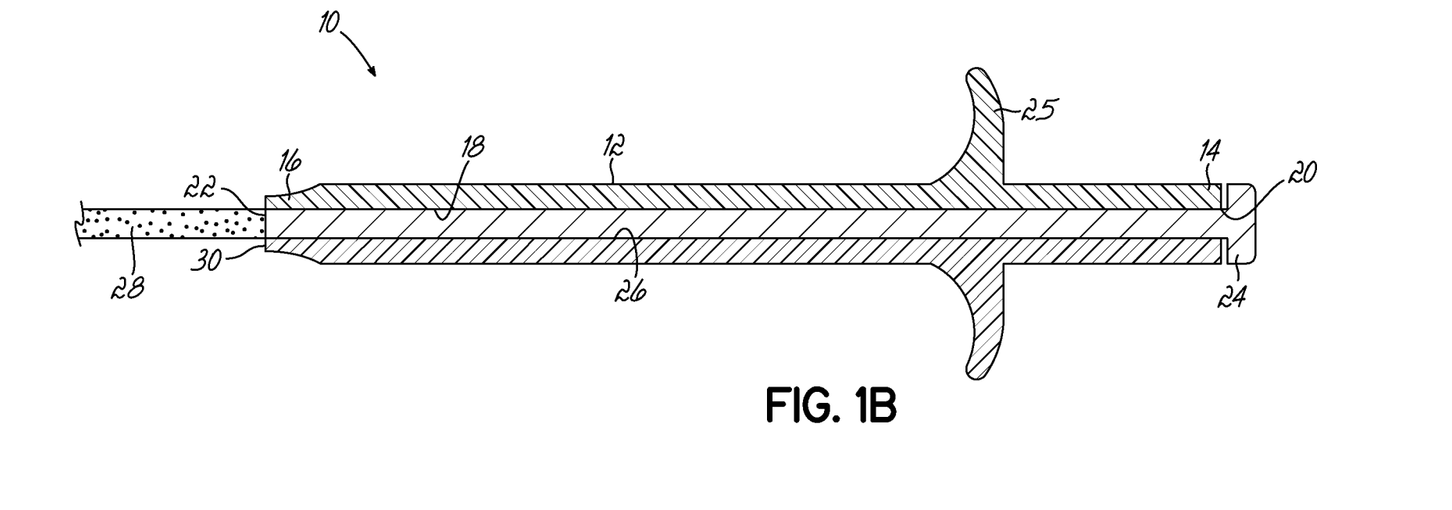
FIG. 1B is a cross-sectional view of the device of FIG. 1A, shown in the second position where a portion of the medical fabric has been dispensed.

Referring to FIGS. 1A and 1B, a device 10 for packing an abscess includes an elongated housing 12 having a proximal end 14, a distal end 16, and a lumen 18 therebetween. The lumen 18 essentially travels between the proximal and distal ends 14, 16 such that there is an opening 20 at the proximal end 14 and an opening 22 at the distal end 16. The device 10 includes an actuator, defined as a plunger 24, that is received in the lumen 18 at the proximal end opening 20 and movable relative to the lumen 18. The device further includes optional finger grips 25. The lumen 18 includes a supply of medical fabric 28, such as gauze, that is situated distally relative to the plunger 24. In order to advance the gauze from the lumen 18 and out of the opening 22, the plunger 24 is advanced axially in the distal direction. The clinician may advance the plunger 24 from the position shown in FIG. 1A to the position shown in FIG. 1B in essentially one pushing movement. Alternatively, the clinician may advance the plunger 24 incrementally to thereby dispense an incremental amount of the gauze 28. The plunger 24 is dimensioned relative to the lumen 18 such that advancement of the plunger 24 displaces the gauze 28 adjacent to the plunger 24, which then forces the downstream gauze 28 out of the opening 22. The configuration of the housing provides that the entire length of the gauze is protected until it reaches the wound site. In order to prevent the gauze 28 from bunching up and getting stuck within the lumen 18 instead of exiting from the opening 22, the inside wall 26 of the lumen 18 may include a lubricious coating. Bunching of the gauze 28 may also be prevented by other certain measures. For example, the gauze 28 may be stored in the lumen 18 in a folded, accordion-like configuration such that a resiliency is imparted to the gauze 28. Such a configuration may provide a spring-like additional force that, in addition to the force from the plunger 24, urges the gauze 28 from the opening 22. Furthermore, the density of the gauze 28 in the lumen 18 may be altered in order to provide for advantageous dispensing of the gauze 28 from the opening 22. For example, increasing the density of the gauze 28 within the lumen 18, such that it is pre-packed, may decrease the likelihood of bunching of the gauze 28. As shown, distal end 16 of device 10 includes a generally flat end 30. However, in one embodiment, the distal end 16 of device 10 may include an atraumatic probe (not shown). The probe may include a shape like the atraumatic distal end of the devices shown in FIGS. 6 and 7. To that end, device 10 may include a generally round or bulbous distal end that is configured to atraumatically remove loculations from the abscess before gauze 28 is packed into the abscess. The housing 12 in this and other embodiments is rigid such that it is sufficiently strong to enable it to be pushed into the body without bending or buckling.

Figure 2A:
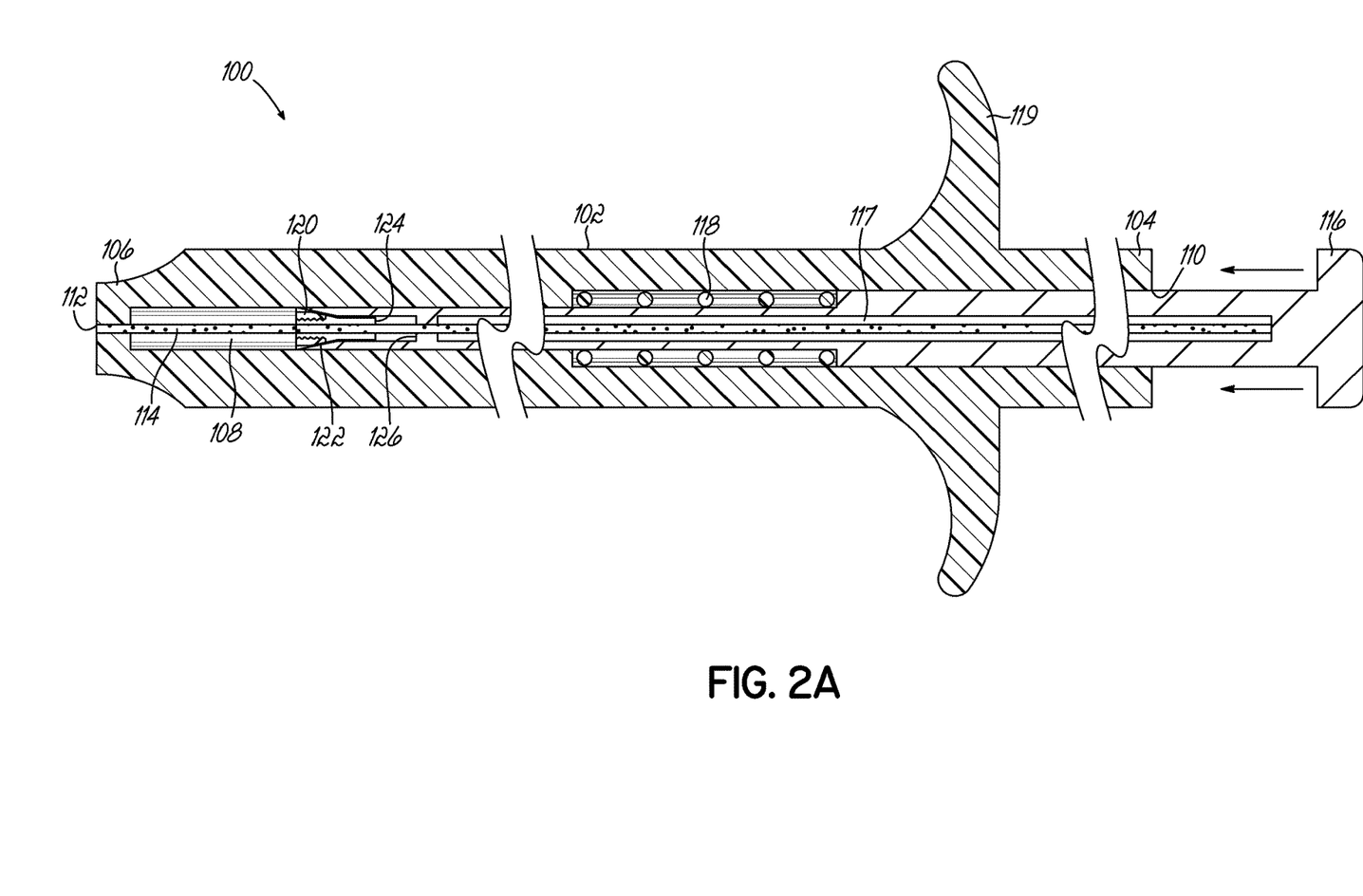
FIG. 2A is a cross-sectional view of an alternative embodiment of a device for directing a medical fabric into a portion of the body, shown in a first position.
Figure 2B:
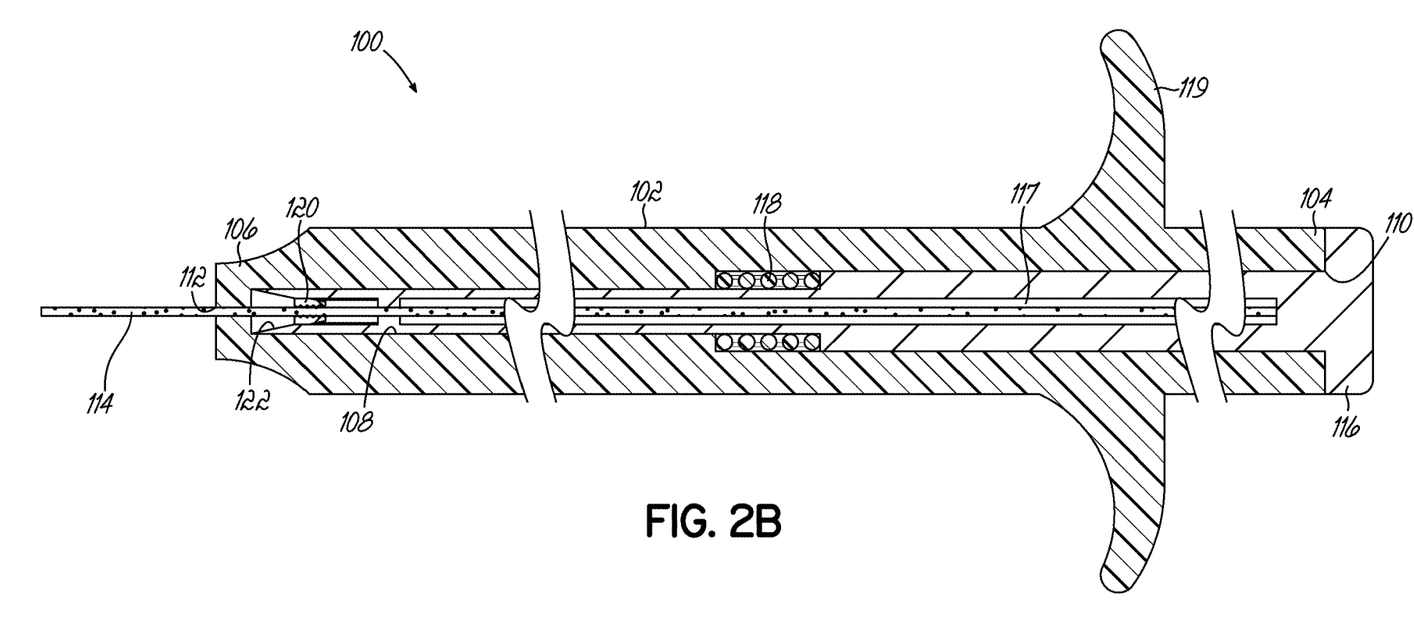
FIG. 2B is a cross-sectional view of the device of FIG. 3, shown in the second position where a portion of the medical fabric has been dispensed.

Referring to FIGS. 2A-2B, an alternative embodiment of a device 100 for packing abscesses is shown. The device 100 includes an elongated housing 102 having a proximal end 104, a distal end 106, and a lumen 108 therebetween. The lumen 108 essentially travels between the proximal and distal ends 104, 106 such that there is an opening 110 at the proximal end 104 and an opening 112 at the distal end 106. As described above, it may be desirable for the clinician to direct metered amounts of gauze 114 into the abscess. In that regard, device 100 includes an actuator, defined as a plunger 116 operatively coupled to a resilient member 118 (i.e., compression spring) and a chuck 120. Normally, as shown in FIG. 2A, the plunger 116 is biased in a proximal position by spring 118, and chuck 120 is in a position radially away from the strip of gauze 114. Plunger 116 also includes a lumen 117 which receives a portion of the gauze 114. Housing 102 includes optional finger grips 119 to assist in moving the plunger 116.

As the plunger 116 is depressed, chuck 120 is forced radially inward by interaction between the chuck 120 and the slanted cam surface 122. Due to the radial inward movement of the chuck 120, the chuck 120 grips the gauze 114. As the plunger moves further distally, the chuck 120 no longer is able to move relative to the housing 102, due at least in part to the interaction of the rear 124 of the chuck 120 with the rear chuck cam surface 126. Therefore, as the plunger 116 moves further distally, so does the chuck 120, and thereby the gauze 114 being gripped by the chuck 120 is also advanced distally out of the opening 112. As the clinician allows the plunger 116 to return to the distal position, spring 118 urges plunger 116 back towards the proximal position. The chuck 120 disengages the gauze 114 after riding the cam surface 122 and moves proximally back to the position shown in FIG. 2A. In order to dispense more gauze 114, the clinician again depresses or clicks the plunger 116 in the distal direction, thereby repeating the above dispensing process until a desired amount of gauze 114 has been dispensed. As with the previous embodiment, the housing 102 protects the entire length of the gauze 114 until it reaches the wound site. The embodiment shown in FIGS. 2A-2B thereby allows the clinician to incrementally dispense a specific, metered amount of gauze 114. The amount of gauze 114 dispensed as shown with one "click" is not limited to that shown and it will be appreciated that each metered dispensing of the gauze 114 may be more or less. Notably, in either of the embodiments shown in FIGS. 1A-2B, once the supply of gauze 114 is exhausted, an additional or supplemental supply of gauze may be reloaded into the device such that the clinician may pack the abscess or other wound with more gauze, if so desired.

Figure 3A:
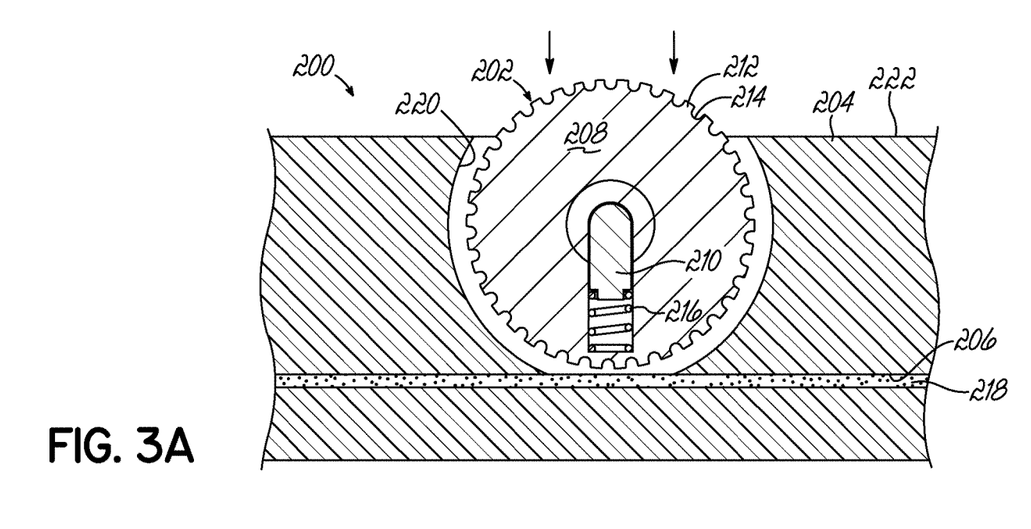
FIG. 3A is a cross-sectional view of an actuator of a device for directing a medical fabric into a portion of the body, shown in a first position.
Figure 3B:
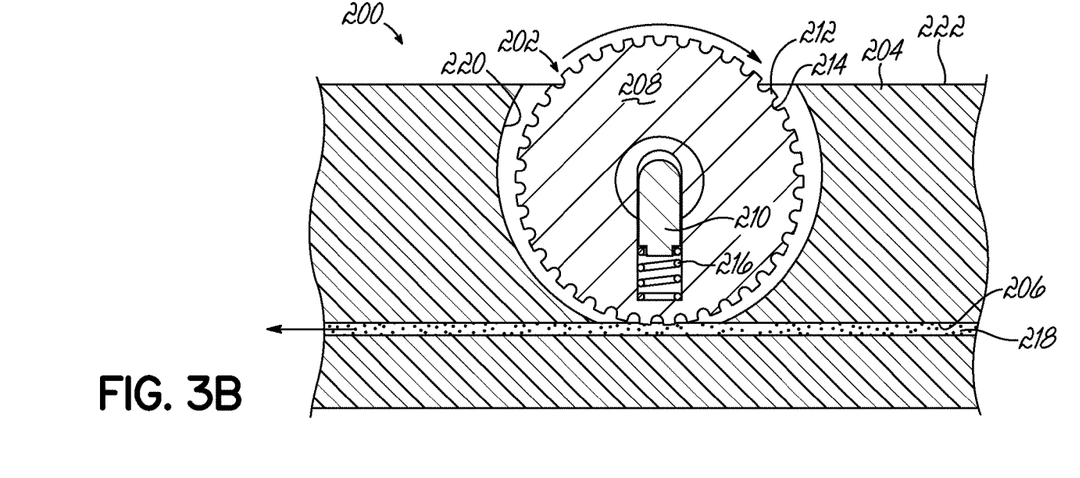
FIG. 3B is a cross-sectional view of the actuator of FIG. 3A, shown in a second position engaging the medical fabric.

A device 200 having an alternative embodiment of an actuator 202 is shown in FIGS. 3A and 3B. A portion of a housing 204 is shown with a space or lumen 206 for receiving a strip or amount of gauze 218. The actuator 202 includes a wheel 208 mounted for rotation on a pin 210. The wheel 208 includes an engaging portion, shown as teeth 212 projecting from the circumferential edge 214 of the wheel 208, that is configured to frictionally engage gauze 218 when the wheel 208 is properly positioned and rotated. In that regard, the pin 210 is mounted to a spring 216 that biases the pin 210 and thus the wheel 208 into a first position whereby the wheel 208 is out of contact, or disengaged from, the gauze 218. Thus, the point of rotation of the wheel 208 is also movable. In the first position (FIG. 3A), therefore, rotation of the wheel 208 does not result in engagement between the teeth 212 and the gauze 218. Of course, the gauze 218 may be thicker or become bunched up at or near the wheel 208 and it is possible that teeth may contact the gauze 218 even when the wheel 208 and/or pin is in the first position. Once the wheel 208 is pushed downward, the pin compresses the spring 216 and the wheel 208 is allowed to move to a second position whereby the teeth 212 may engage the gauze 218. Once the gauze 218 is rotated in the clockwise direction, the gauze 218 may be directed distally out of the opening (not shown) of the device 200. Notably, the wheel 208 resides in an aperture 220 of the housing 204 and extends above an upper surface or edge 222 of the housing 204 such that a clinician may access the wheel 208.

Figure 4:
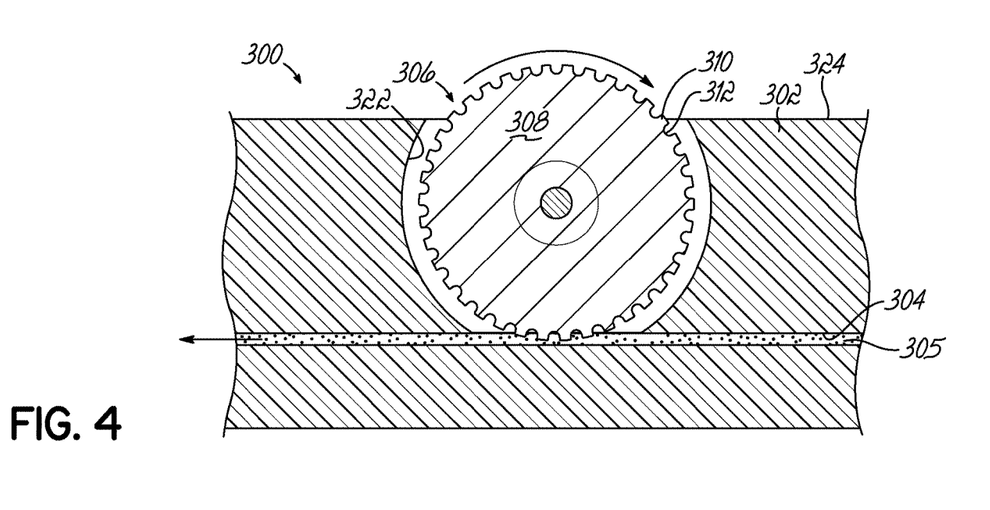
FIG. 4 is an alternative embodiment of an actuator of a device for directing a medical fabric into a portion of the body.
Figure 5:
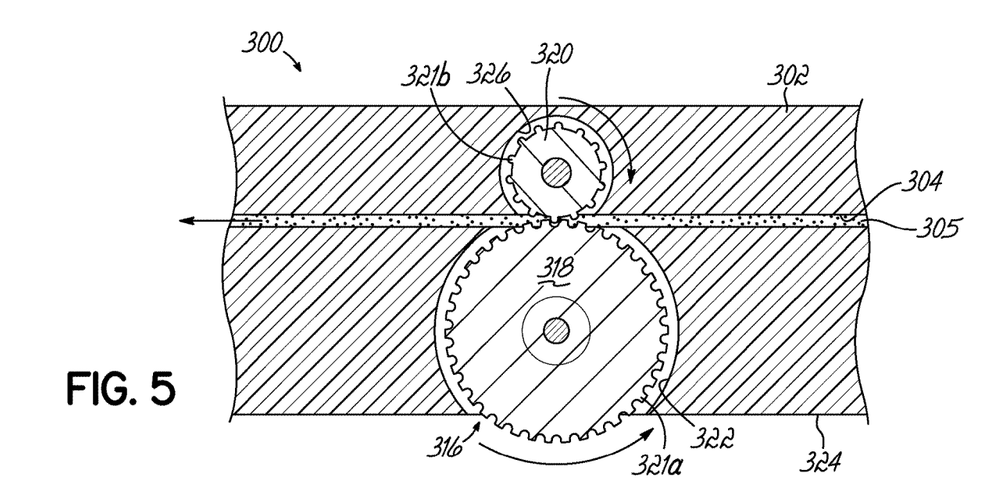
FIG. 5 is another alternative embodiment of an actuator of a device for directing a medical fabric into a portion of the body.

Devices with similar but alternative embodiments of actuators are shown in FIGS. 4 and 5. FIG. 4 shows a portion of a device 300 having a housing 302, and a lumen 304 for accepting gauze 305. The actuator 306 is defined as a single wheel 308 including teeth 310 extending from the circumferential edge 312 of wheel 308. The wheel 308 is stationary such that the axis of rotation is stationary. Similar to the above embodiment, due to the engagement of the teeth 310 with the gauze 305, clockwise rotation of wheel causes the gauze 305 to be directed in the distal direction. Referring to FIG. 5, where same or similar structures to those in FIG. 4 are marked with the same reference numerals, the actuator 316 includes a first wheel 318 and a second wheel 320. Teeth 321a of the first wheel are configured to essentially mesh with teeth 321b of second wheel 320. Rather than relying on friction between one wheel and the gauze, the embodiment of FIG. 5 relies on the gauze 305 being essentially pinched between the first and second wheels 318, 320. As shown, the rotation of the first wheel 318, as would be driven by a user in the counter-clockwise direction, causes the clockwise rotation of the second wheel 320. Therefore, because the gauze 305 is pinched between the first and second wheels 318, 320, the rotation of the wheels 318, 320 as shown causes the distal advancement of the gauze 305. Notably, in each of these embodiments, as in FIGS. 3A-3B, wheel 308 and first wheel 318 both reside in an aperture 322 in the housing 302 and extend to a point outside of the housing 302 outward of the edge 324 such that a user may access the wheel 308 and first wheel 318, respectively. Second wheel 320 also resides in an aperture 326.

The embodiments as shown in FIGS. 3A-5 are illustrative of examples where rotational movement of, for example, a wheel (or wheels) frictionally engages the gauze. Specifically, the embodiments shown include at least one wheel that is rotatable about an axis that is transverse to, more specifically, perpendicular to, the axis along which the gauze travels, as well as the longitudinal axis of the housing. The sizes of the wheels, for example, may be larger or smaller than those shown. Furthermore, it is anticipated that these and other rotationally driven actuator embodiments may be included in various types of housings. For example, the housing of any embodiment may be shaped like a "gun" such that the wheel may be operated by the index or middle finger and include a handle transverse to the axis where the gauze is dispensed. Alternatively, the housing may be a generally axially oriented, and/or an essentially elongated or continued version of that shown in FIGS. 3A-5, where the clinician may use his or her thumb or other finger in order to drive the wheel and advance the gauze.

Figures 6, 6A:
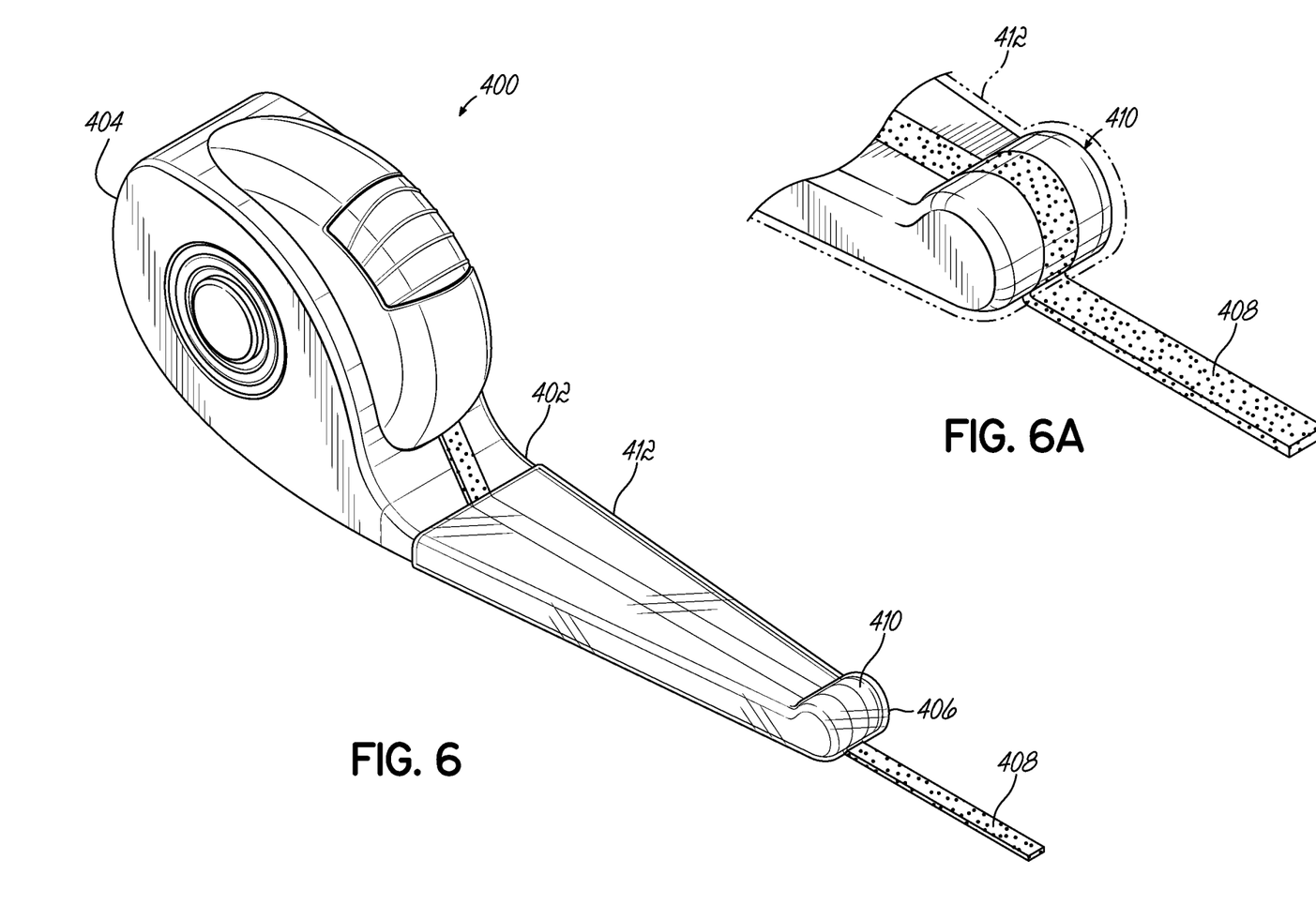
FIG. 6 is an alternative embodiment of a device for directing a medical fabric into a portion of the body.
FIG. 6A is a detailed perspective view of the device of FIG. 6.

FIG. 6 shows an alternative embodiment of a device 400 for packing an abscess. The device 400 includes an elongated housing 402 with a proximal end 404 and a distal end 406. The distal end 406 includes an opening (not shown) that allows the gauze 408 to exit therefrom as it is driven distally. Referring also to FIG. 6A, the distal end 406 further includes a probe 410 for atraumatically removing loculations in an abscess. As shown, the probe 410 has a generally bulbous shape such that a cross sectional dimension thereof is larger than a cross sectional dimension of a more proximal portion. Moreover, probe 410 includes a rounder, bulbous shape relative to the rest of the device. The device 400 includes at least one wheel or other rotational member (not shown) within the housing 402 that may operate similarly to the other embodiments as described herein to drive the gauze 408 out of the opening. Rather than traveling through a lumen, the gauze exits from the proximal end portion of the housing 402. The housing 402 includes an optional cover 412 along a top portion thereof and is provided to protect the gauze 408 as it travels along the shaft and exits from the opening.

Figure 7:
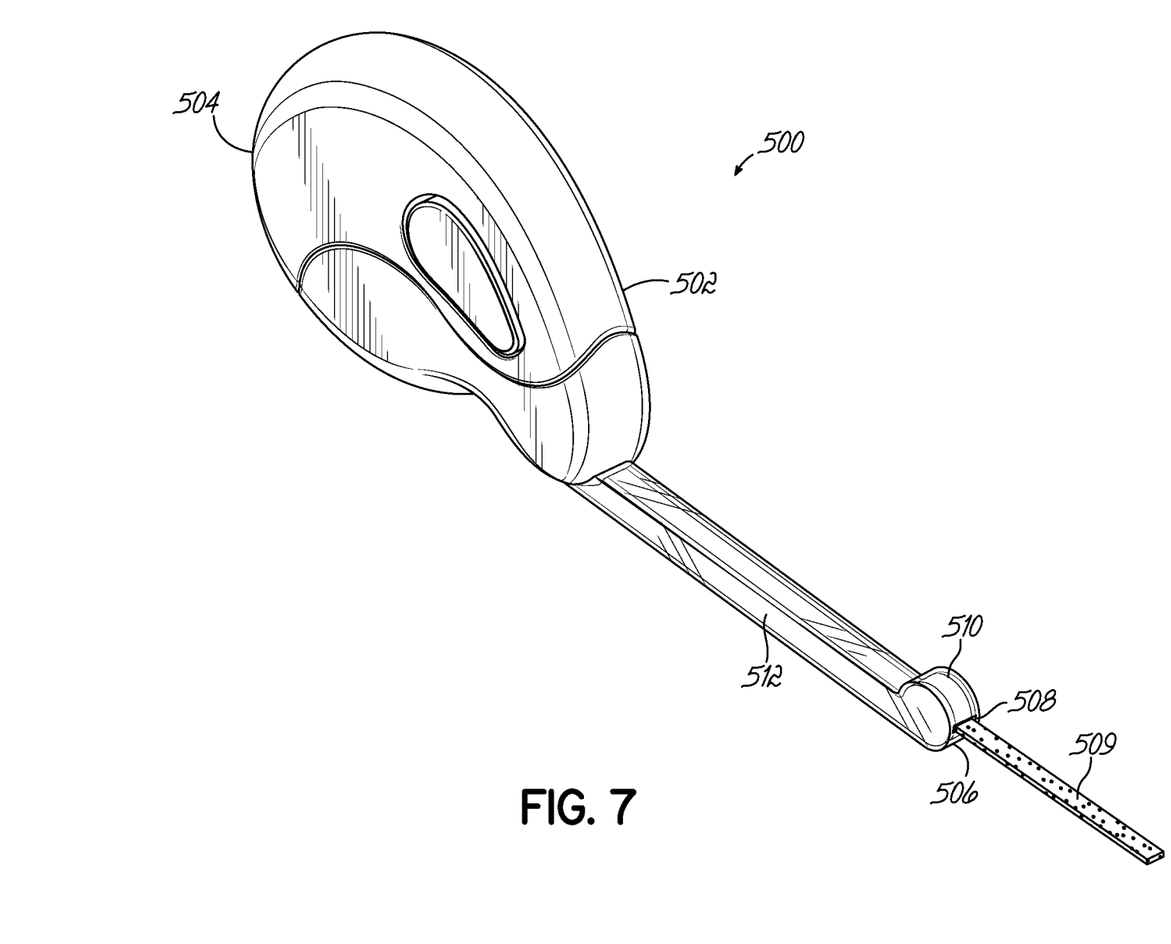
FIG. 7 is another alternative embodiment of a device for directing a medical fabric into a portion of the body.

FIG. 7 shows yet another alternative embodiment of a device 500 for packing an abscess. The device 500 includes a housing 502 with a proximal end 504 and a distal end 506 shaft having a cover 510 therebetween. The distal end 506 includes an opening 508 that allows the gauze 509 to exit therefrom as it is driven distally. The distal end 506 further includes a probe 512 for atraumatically removing loculations in an abscess. The device 500 includes at least one wheel or other rotational member (not shown) within the housing 502 that may operate similarly to the other embodiments as described herein to drive the gauze out of the opening 508.

In an alternative embodiment, the engaging portion of a wheel or other rotational member may be defined as an alternative feature, so long as the engaging portion is configured to frictionally engage the gauze to advance it along the lumen and out of the opening. By way of example, the engaging portion may include a rubber strip or other frictional material, instead of teeth, that may frictionally engage the gauze as it moves, or rotates, relative to the gauze. Moreover, rather than being manually actuated by a user, any of the actuators disclosed herein may be alternatively driven by a motor.

The internal compartment may also include a structure for controlling the dispensing of the gauze. For example, the internal compartment may include a mechanism, such as one or more gears that rotate a cartridge with a rolled sterilized gauze strip. The mechanism may also function as a brake to prevent the rotation of the cartridge. The dispensing and optional braking mechanism may also include a structure for activating the mechanism. In an embodiment, the activating structure is a thumbwheel. In another embodiment, the activating structure is a button. The device may also include a release element that allows the sterilized gauze strip to be quickly dispensed from the housing.

Any embodiment of the device as disclosed herein may be manufactured in a variety of sizes such that it may be used for various sizes of abscesses that require different amounts of gauze. For example, the clinician may recognize that a certain size of abscess will require a certain amount of gauze. Rather than having to cut certain lengths of gauze as essentially required in the grab and push method, the clinician may simply select the appropriate size device and direct the entire supply of gauze into the abscess in the manner described herein. In any of the embodiments described herein, the supply of gauze may be situated proximally to the actuator, i.e., upstream of the wheel or other actuators described herein.

The gauze may be loaded into the housing at the clinical environment or may alternatively be pre-loaded into the housing prior to packaging and use in the clinical environment. In that regard, there are several storage configurations of the gauze that are possible. For example, the gauze may be rolled up within a storage portion of the housing like a roll of tape or yarn. Alternatively, the gauze may be configured into several pieces with interlocking folds, such as c-folds that are used with facial tissues or stacked paper towels. Regardless of the configuration of the gauze, in any of the embodiments described herein, the device may be configured such that after the supply of gauze is exhausted from the housing, an additional supply of gauze may be added to the housing. For example, a portion of the housing may be removable such that an additional roll, for example, may be directed into the housing. Gauzes having various materials, sizes, weave patterns, and thicknesses, etc., are able to be used with the disclosure as described herein. Moreover, the disclosure herein is not limited to gauze. The devices and methods as described herein may be used with other medical fabrics or tapes for a variety of procedures not limited to packing abscesses. For example, the device may be used in situations or procedures involving other areas of fluid collection, such as seroma. Embodiments of the device are constructed of materials, such as plastic or other polymeric material, which are safe for intimate contact with a subject and may be made using routine methods as are known to those of ordinary skill in the art. While plastic and polymeric materials are described, materials such as metal, glass, ceramic, and other materials as are known to those of skill in the art may be used.

While the present invention has been illustrated by a description of various preferred embodiments and while these embodiments have been described in some detail, it is not the intention of the Applicants to restrict or in any way limit the scope of the appended claims to such detail. Additional advantages and modifications will readily appear to those skilled in the art. The various features of the invention may be used alone or in any combination depending on the needs and preferences of the user. This has been a description of the present invention, along with the preferred methods of practicing the present invention as currently known. However, the invention itself should only be defined by the appended claims.

What is claimed is:

1. A device for directing a medical fabric into a portion of a body, comprising: an elongated housing having a distal end and an opening at the distal end; a supply of medical fabric in the housing; an actuator spaced from said opening, said actuator including a wheel that resides in an aperture in the housing and extends to a point outside of said housing to be accessed by a user to advance a portion of the medical fabric through said housing and out of the opening and the supply of medical fabric is upstream of the wheel.

2. The device of claim 1, wherein the actuator is configured to frictionally engage the medical fabric.

3. The device of claim 1, wherein rotational movement of the actuator advances the medical fabric towards the distal end.

4. The device of claim 3, wherein a rotational axis of the actuator is substantially perpendicular to an axis along which the medical fabric advances.

5. The device of claim 1, wherein the actuator is movable between a first position where an engaging portion of the actuator is positioned away from the medical fabric and a second position where the engaging portion is positioned to engage the medical fabric.

6. The device of claim 5, further comprising a biasing member coupled with the actuator and configured to bias the actuator towards the first position.

7. The device of claim 1, wherein friction between the actuator and the medical fabric during movement of the actuator advances the medical fabric.

8. The device of claim 1, wherein the wheel includes at least one projecting portion configured to engage the medical fabric.

9. The device of claim 1, wherein the supply of medical fabric is in a rolled configuration.

10. The device of claim 1, wherein the supply of medical fabric is in a folded configuration.

11. The device of claim 1, wherein the supply of medical fabric is positioned proximal to the actuator.

* * * * *

UNITED STATES PATENT AND TRADEMARK OFFICE
CERTIFICATE OF CORRECTION

Page 1 of 2

PATENT NO. : 10,945,894 B2
APPLICATION NO. : 14/434544
DATED : March 16, 2021
INVENTOR(S) : Privitera et al.

It is certified that error appears in the above-identified patent and that said Letters Patent is hereby corrected as shown below:

On the Title Page

Replace the title page with the attached title page showing the corrected number of claims.

In the Claims

Column 8, Line 20 Claims 12 and 13, insert --12. The device of claim 1 further comprising a line dispensing mechanism between the wheel and the medical fabric.
13. The device of claim 12 wherein the dispensing mechanism includes one or more gears.--

Signed and Sealed this
Sixteenth Day of November, 2021

Drew Hirshfeld
*Performing the Functions and Duties of the*
*Under Secretary of Commerce for Intellectual Property and*
*Director of the United States Patent and Trademark Office*

(12) United States Patent
Privitera et al.

(10) Patent No.: US 10,945,894 B2
(45) Date of Patent: Mar. 16, 2021

(54) DEVICES AND METHODS FOR DIRECTING A MEDICAL FABRIC INTO A PORTION OF THE BODY (71) Applicant: University of Cincinnati, Cincinnati, OH (US)

(72) Inventors: Mary Beth Privitera, Mason, OH (US); Arthur Pancioli, Mason, OH (US)

(73) Assignee: University of Cincinnati, Cincinnati, OH (US)

(*) Notice: Subject to any disclaimer, the term of this patent is extended or adjusted under 35 U.S.C. 154(b) by 652 days.

(21) Appl. No.: 14/434,544

(22) PCT Filed: Oct. 9, 2013

(86) PCT No.: PCT/US2013/064086
§ 371 (c)(1),
(2) Date: Apr. 9, 2015

(87) PCT Pub. No.: WO2014/058992
PCT Pub. Date: Apr. 17, 2014

(65) Prior Publication Data
US 2015/0283005 A1    Oct. 8, 2015

Related U.S. Application Data (60) Provisional application No. 61/711,480, filed on Oct. 9, 2012.

(51) Int. Cl.
A61F 15/00 (2006.01)
A61F 13/38 (2006.01)
(Continued)

(52) U.S. Cl.
CPC ......... *A61F 15/001* (2013.01); *A61F 13/38* (2013.01); *A61F 15/002* (2013.01); *A61F 2013/00302* (2013.01); *A61F 2013/2014* (2013.01)

(58) Field of Classification Search
CPC ...... A61F 15/001; A61F 15/002; A61F 13/38; A61F 2013/00302; A61F 2013/2014
See application file for complete search history.

(56) References Cited

U.S. PATENT DOCUMENTS 5,263,927 A * 11/1993 Shlain ............ A61B 17/00234
604/13
7,837,705 B2  11/2010 White et al.
(Continued)

FOREIGN PATENT DOCUMENTS

| EP | 0604101 A1 | 6/1994 |
| WO | 93/08740 A1 | 5/1993 |
| WO | 01/21058 | 3/2001 |

OTHER PUBLICATIONS

International Searching Authority, International Search Report and Written Opinion in corresponding Application No. PCT/US2013/064086, dated Jan. 22, 2014 (10 pages).
(Continued)

*Primary Examiner* — Benjamin J Klein
(74) *Attorney, Agent, or Firm* — Wood Herron & Evans LLP (57) ABSTRACT

A device (10) for directing a medical fabric (28) into a portion of a body. An elongated housing (12) having a distal end (16) and an opening (22) at the distal end (16). A supply of medical fabric (28) in the housing (12). An actuator (24) spaced from said opening (22) and configured to advance a portion of the medical fabric (28) through said housing (12) and out of the opening (22).

13 Claims, 7 Drawing Sheets